United States Patent [19]

Kurkov

[11] 4,113,735

[45] Sep. 12, 1978

[54] PROCESS FOR THE PRODUCTION OF N-ACETYL-2-PYRROLIDONE

[75] Inventor: Victor P. Kurkov, San Rafael, Calif.

[73] Assignee: Chevron Research Company, San Francisco, Calif.

[21] Appl. No.: 750,310

[22] Filed: Dec. 13, 1976

[51] Int. Cl.[2] .......................................... C07D 207/00
[52] U.S. Cl. .......................................... 260/326.5 FL
[58] Field of Search ............. 260/326.5 FL, 326.5 FN

[56] References Cited

U.S. PATENT DOCUMENTS 3,714,185  1/1973  McCoy et al. ............. 260/326.5 FN

FOREIGN PATENT DOCUMENTS 1,027,949  5/1966  United Kingdom.

Primary Examiner—Jose Tovar
Attorney, Agent, or Firm—Dix A. Newell; Thomas G. DeJonghe; Lawrence S. Squires

[57] ABSTRACT

A process for producing N-acyl-2-pyrrolidone which comprises contacting N-acyl allylamine with carbon monoxide in the presence of an aliphatic carboxylic acid solvent and a homogeneous catalyst of palladium or platinum coordinated with triphenylphosphine. According to a preferred embodiment, the acyl group is removed from the N-acyl-2-pyrrolidone by contacting and heating the N-acyl-2-pyrrolidone with allylamine to thereby effect transacylation and obtain product 2-pyrrolidone and N-acyl-allylamine as a recycle feed stream. Alternatively, N-acyl-2-pyrrolidone can be hydrolyzed to 2-pyrrolidone and the carboxylic acid derived from the acyl group.

5 Claims, No Drawings

PROCESS FOR THE PRODUCTION OF N-ACETYL-2-PYRROLIDONE

BACKGROUND OF THE INVENTION

The present invention relates to the preparation of 2-pyrrolidone and N-acyl-2-pyrrolidone. The 2-pyrrolidone is useful for making synthetic fibers such as nylon fiber.

Prior art methods for producing pyrrolidone include the reaction of maleic anhydride with ammonia and hydrogen — see U.S. Pat. No. 3,109,055; the reaction of succinic anhydride with ammonia and hydrogen — see U.S. Pat. No. 3,080,077; and the reaction of gamma-butyrolactone with ammonia — see U.S. Pat. No. 3,115,500.

It has also been disclosed that 2-pyrrolidone can be made by the reaction of allylamine with carbon monoxide using a cobalt catalyst — see British Pat. No. 628,659 and Falbe et al., Chem. Ber. 98, 1928 (1965). British Pat. No. 1,028,097 states that it improves on the yields achieved in British Pat. No. 628,659 by using relatively large amounts of solvent — that is, large parts of benzene or the like solvent per part of the allylamine feed. The British Pat. No. 1,028,097 patent reports a yield of 27 weight percent 2-pyrrolidone using one part benzene solvent per one part allylamine and a yield of 54% when using 30 parts by weight benzene per one part by weight allylamine at a temperature of 280° C and 300 atmospheres pressure. The British Pat. No. 1,028,097 states at pages 2–3:

"The catalyst used in the process according to the invention is a cobalt carbonyl compound. According to the U.K. patent specification No. 628,659 hydrogenation catalysts, for example nickel, may be used. It was found, however, that good yields of alpha-pyrrolidone can only be obtained with cobalt catalsyts."

Another patent disclosing cyclocarbonylation of allylamine to 2-pyrrolidone is U.S. Pat. No. 3,714,185. U.S. Pat. No. 3,714,185 states that the prior art suggested to catalyze the cyclocarbonylation of allylamine to 2-pyrrolidone with salts such as the halides, acetates and nitrates or carbonyls of cobalt, rhodium, nickel, iron, platinum and palladium.

According to U.S. Pat. No. 3,714,185, a rhodium or cobalt catalyst is used for the cyclocarbonylation reaction. The U.S. Pat. No. 3,714,185 discloses the use of a wide range of ligands for the catalyst including phosphine ligands such as triphenylphosphine. The U.S. Pat. No. 3,714,185 also mentions that it is an object of the U.S. Pat. No. 3,714,185 process to provide a new method for the carbonylation of allylamines, allylamides and allylalcohols to produce the corresponding lactams, imides and lactones, respectively. The reaction temperature disclosed in the U.S. Pat. No. 3,714,185 are 120°–290° C and preferably 150°–200° C.

SUMMARY OF THE INVENTION

According to the present invention a process is provided for producing N-acyl-2-pyrrolidone, which process comprises contacting N-acyl-allylamine with carbon monoxide and a homogeneous catalyst of palladium or platinum coordinated with a phosphine having at least one aryl group attached to phosphorus. Preferably, the phosphine is triphenylphosphine.

The reaction can be carried out at a temperature between 25° and 250° C and a carbon monoxide partial pressure between 100 and 10,000 psig. However, one of the advantages of the present invention is that I have found that the present reaction can be carried out while achieving high yields of the N-acyl-2-pyrrolidone at relatively mild conditions, particularly including low temperatures such as about 120° and carbon monoxide partial pressure of about 1000 psig. Suitable relatively mild temperatures include a temperature range of 50° to 200° C, more preferably 70° to 170° C, and carbon monoxide partial pressures between 100 and 7500 psig, more preferably 500 to 5000 psig.

Among other factors, the present invention is based on my findings that N-acyl allylamine is carbonylated with carbon monoxide to N-acetyl-2-pyrrolidone in high yields when using a specific catalyst, namely a homogeneous palladium or platinum catalyst coordinated with a phosphine ligand containing at least one aryl group. Moreover, as previously indicated, the high yields — that is, yields above 40% and as high as 60–70% — are achieved by the present process at relatively mild temperatures of about 120° C or temperatures in that vicinity, which is relatively mild compared to prior art temperatures used for carbonylation of allylamine.

Surprisingly, when I attempted to cyclocarbonylate allylamine using the above-mentioned palladium catalyst, virtually no yield was obtained under conditions wherein high yields of N-acyl-2-pyrrolidone were found by me when using the N-acyl allylamine feedstock.

Also, surprisingly I have found that the process of the present invention is quite sensitive to the solvent in the presence of which the N-acyl allylamine is carbonylated with carbon monoxide. Thus, as will be seen from the examples hereinbelow, when using an aliphatic carboxylic acid solvent relatively high yields of about 45% N-acyl-2-pyrrolidone were obtained versus yields of about 11% or lower when using other solvents such as toluene, acetonitrile and dimethyl-acetamide. In particular, I have found that acetic acid is an especially advantageous solvent for the process of the present invention when carbonylating N-acetyl-allylamine to N-acetyl-2-pyrrolidone.

The process of the present invention can also be carried out neat, that is, in the absence of an added solvent such as the preferred acetic acid solvent. When the reaction of the present invention is carried out neat, preferably an excess of the phosphine, such as the triphenylphosphine, is used. Thus, typically when carrying out the reaction of the present invention neat, between 10 and 200 or more mols of phosphine is used per mol of palladium or platinum catalyst with the N-acyl-allylamine feed dissolved in the phosphine. Thus the excess phosphine, such as excess triphenylphosphine, serves not only as the ligand for the palladium or platinum but also effectively as the solvent for the reaction. The preferred reaction temperatures are those sufficient to maintain the phosphine solvent molten, for example above about 80° C and below about 250° C.

Whether the reaction is carried out with or without added solvent, the amount of phosphine ligand relative to the palladium or platinum metal is important in the present invention. The ligand to metal ratio should be at least 2, more preferably 8–20 and can be as high as 200 and more.

The phosphine ligand used in the present invention can be denoted with a general formula as follows:

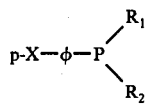

where $R_1$ and $R_2$ are aryl, substituted aryl or alkyl group with 1–10 carbon atoms. $pX-\phi$ is an aryl group with a para substituent X. X can be H, $C_1$–$C_{10}$ alkyl group or $C_1$–$C_{10}$ alkoxy group.

The palladium catalyst (and similarly the platinum catalyst) used in the present invention preferably is added to the reaction zone in the form of palladium salt, but it may also be added as a palladium complex or palladium metal. The oxidation state of palladium can be either +2 or 0; the higher oxidation stage of palladium is probably reduced to 0 under the reaction conditions. Examples of suitable palladium salts are:
  palladium chloride,
  palladium bromide,
  palladium iodide,
  palladium oxide,
  palladium acetate,
  palladium octanoate,
  palladium 2-ethylhexanoate,
  palladium naphthenate and
  palladium nitrate.
Examples of suitable complexes are:
  palladium acetylacetonate,
  bistriphenylphosphine-palladium-chloride,
  tetrakistriphenylphosphine-palladium, and
  bisbenzonitrile-palladium-chloride.

Preferably the palladium salt is a palladium halide, namely palladium chloride, fluoride, iodide or bromide. Preferably the palladium salt is in the form of $Pd^{+2}$ and particularly preferred is palladium chloride as $PdCl_2$.

Preferably the acyl group of the N-acyl-allylamine is a $C_2$–$C_{10}$ aliphatic acyl group. Preferably the aliphatic acid solvent is a $C_2$–$C_{10}$ acid. It is particularly preferred that the acyl group is acetyl. Also it is particularly preferred that the aliphatic acid solvent is acetic acid.

According to a preferred embodiment of the present invention, an advantageous process is provided for producing N-acetyl-2-pyrrolidone from allylamine, which process comprises: (a) reacting allylamine with acetic acid to thereby obtain acetyl allylamine; and (b) contacting the acetyl allylamine with a triphenylphosphine-coordinated palladium catalyst and carbon monoxide in the presence of acetic acid in a reaction zone and in the absence of water in the reaction zone, at a temperature between 50° and 200° C and a carbon monoxide partial pressure above 100 psig to thereby obtain N-acetyl-2-pyrrolidone.

The preferred embodiment of the present invention, as mentioned above, can be carried out in one reaction zone wherein the allylamine is converted in situ to N-acetyl-allylamine. However, I have found that higher yields are obtained when the steps (a) and (b) of the above embodiment are carried out in separate reaction zones wherein the N-acetyl-allylamine produced in accordance with step (a) is used as the feedstock for step (b).

In either event, I have found that it is important to avoid the presence of a substantial amount of water when carrying out the carbonylation of the N-acetyl-allylamine to obtain N-acetyl-2-pyrrolidone. I have found that the presence of water inhibits the carbonylation reaction of the present invention. Thus, the amount of water present during the carbonylation reaction of the present invention should be less than about 5% by weight of water based on N-acetyl-allylamine, preferably less than 1% water based on N-acetyl-allylamine.

In the separate-zone process wherein allylamine is first reacted with acetic acid, water formed in the reaction can be removed from the reaction product N-acetyl-allylamine by distillation prior to feeding the N-acetyl-allylamine to the carbonylation step.

For carrying out both steps of the reaction in one reaction zone or one reaction vessel wherein the N-acetyl-allylamine is generated in situ, I have found that acetic acid anhydride is advantageous in effectively acetylating allylamine without generating water which inhibits the cyclocarbonylation reaction. In this embodiment wherein acetic acid anhydride is used to effectively take up or remove the water, the amount of acetic acid anhydride preferably is adjusted so that there is at least sufficient acetic acid anhydride on a molar basis compared to the mols of water to take up or remove the mols of water formed.

Thus, in accordance with a preferred embodiment of the present invention, steps (a) and (b) of the embodiment mentioned above are carried out in one reaction zone and in the presence of acetic acid anhydride sufficient to acetylate allylamine to N-acetyl-allylamine and to maintain anhydrous conditions.

According to another preferred embodiment of the present invention, I have found that a particularly advantageous over-all process for producing 2-pyrrolidone from allylamine is provided as follows: (a) contacting N-acetyl-allylamine with a triphenylphosphine-coordinated palladium catalyst and carbon monoxide in the presence of acetic acid and in the absence of water in a reaction zone, at a temperature between 50° and 200° C and at a carbon monoxide partial pressure above 100 psig, to thereby obtain N-acetyl-2-pyrrolidone, (b) heating the N-acetyl-2-pyrrolidone from step (a) with allylamine at a temperature of 50° to 200° C to thereby transfer the acetyl group from the N-acetyl-2-pyrrolidone to the allylamine and obtain N-acetyl-allylamine, and (c) separating 2-pyrrolidone from the reaction product of step (b) and recycling the remaining N-acetyl-allylamine as feed to step (a).

EXAMPLES

The following examples summarize exemplary data illustrating the process of the present invention. Table I contains data relevant to the effect of the ratio of triphenylphosphine to palladium in the reaction of the present invention, that is, the cyclocarbonylation of N-acetyl-allylamine to produce N-acetyl-2-pyrrolidone. In Table I, the first column indicates the amount of phosphine used. The triphenylphosphine is abbreviated $\phi_3 P$.

The second column in Table I is the ratio of the amount of phosphine ligand (abbreviated as L in the table) to the amount of palladium, Pd. The third column is the reaction time in hours; the fourth column is the percent conversion of N-acetyl-allylamine; and the fifth column is the selectivity in mol percent of N-acetyl-2-pyrrolidone from the converted N-acetyl-allylamine feed. The last two columns in the table are the identification number and the example number.

The data for Table I were generated using a 625-cc steel pressure vessel charged with reactants, solvent and catalyst, as indicated at the bottom of Table I. Thus there were charged to the reactor 100 ml of acetic acid solvent, 0.5 mol of N-acetyl-allylamine, 3.59 mmols of palladium chloride and an amount of triphenylphosphine as indicated in tabular form in Table I. The reactor was pressured with 500 psig carbon monoxide, heated to 120° C and the pressure was then adjusted to 1500 psig with additional carbon monoxide. The reactor contents were mixed by rocking. The carbon monoxide pressure was maintained constant at 1500 psig for 2 hours.

The reactor was then cooled to room temperature and depressurized. The contents were analyzed by gas chromatography so as to determine the amount of feed and N-acetyl-allylamine converted and to determine the selectivity of N-acetyl-2-pyrrolidone based on the mols of N-acetyl-allylamine converted.

The procedures used to generate the data tabulated in the other tables are similar to the procedure used to generate the data tabulated in Table I. As with Table I, the reactor charge used for the examples tabulated is listed at the bottom of the respective tables.

As shown by Table II, various phosphines can be used as ligands of the catalyst used in the process of the present invention. Aryl phosphines are the preferred ligands for the catalyst and triphenylphosphine is the most preferred phosphine component for the catalyst used in the present invention. In general, the phosphine component of the catalyst must have an aryl group such as phenyl or a lower alkyl-substituted phenyl. Thus, in broad terms, the catalyst used in the present invention can be defined as one wherein the palladium or platinum is coordinated with a phosphine containing at least one aryl group. As can be seen from I.D. number B2463-47, when an alkoxy group, namely ethoxy, was attached to phosphorus, no yield of N-acetyl-2-pyrrolidone was obtained. Thus the terminology "phosphine containing at least one aryl group" is used in the present application to exclude phosphines wherein an alkoxy group is attached directly to the phosphorus of the phosphine.

Table III gives experimental data showing that when the feed to the present invention is allylamine, zero yield of 2-pyrrolidone is obtained. This is in contrast to Example 18 in Table III, wherein when the feed was N-acetyl-allylamine a yield of 45.2 mol percent N-acetyl 2-pyrrolidone was obtained. Thus, the importance of the substituent acyl group on the nitrogen of the feed material is shown to be unexpectedly important for the process of the present invention. Example 19 in Table III shows that even when using the N-acetyl-allylamine feed if no phosphine component is used in the catalyst system, that is if only palladium component of the catalyst is used, zero yield of N-acetyl-2-pyrrolidone is obtained.

Table IV contains data on the effect of solvent used in the process of the present invention. As is seen from the selectivity data of Table IV, an aliphatic carboxylic acid, namely acetic acid, resulted in far higher yields than when using other solvents.

Table V shows results for the use of different phosphine ligands with the palladium component of the catalyst. Examples 24 and 25 show particularly advantageous results when using triphenylphosphine as the ligand material. Examples 26 and 27 show the results where the phosphine contains at least 1 aryl group and other organic substituents; in the case of Examples 26 and 27, the other organic substituent was N-butyl and two phenyl groups were attached to the phosphorus rather than three phenyl groups as in the case of triphenylphosphine. As shown in Examples 29 through 32, the aryl group of the phosphine can be substituted in the para position with alkyl and alkoxy substituent. Although Example 28 illustrates that an alkoxy group such as ethoxy attached to the phosphorus results in zero yield of the desired N-acetyl-2-pyrrolidone product. Example 33 shows the criticality of the aryl group being attached directly to the phosphorus atom for the tribenzylphosphine gave 0% yield of N-acetyl-2-pyrrolidone.

Table VI shows results for various catalysts. Table VII shows results for the cyclocarbonylation reaction using only the phosphine and no added solvent such as acetic acid. Table VIII shows data for cyclocarbonylation of various substituted allylamines and also shows the use of chloroplatinic acid as an effective catalyst in an alternate embodiment of the present invention.

TABLE I

CARBONYLATION OF N-ACETYL-ALLYLAMINE
EFFECT OF $\phi_3$P/Pd RATIO

| Phosphine, mmol | | L/Pd | Time, Hours | Conv.,% | Selectivity Mol % | I.D. No. | Ex. No. |
|---|---|---|---|---|---|---|---|
| $\phi_3$P | 50 | 20 | 2 | 90.0 | 66.6 | B2408-09 | 1 |
| $\phi_3$P | 50 | 20 | 2 | 82.8 | 64.5 | B2408-10 | 2 |
| $\phi_3$P | 30 | 12 | 2 | 80.8 | 63.1 | B2408-08 | 3 |
| $\phi_3$P | 20 | 8 | 2 | 89.6 | 53.0 | B2408-05 | 4 |
| $\phi_3$P | 9.2 | 3.7 | 2 | 95.7 | 45.2 | B2352-39* | 5 |
| $(\phi_3P)_2PdCl_2$ | 2.5 | 2.0 | 2 | 89.3 | 29.3 | B2408-06 | 6 |
| None | 0 | 0 | 2 | 7.0 | 0 | B2352-49 | 7 |

*Included for comparison — charge contained hydroquinone

Reactor charge:
- Acetic acid — 100 ml
- N-acetyl-allylamine — 0.5 mol
- Benzene — 30 ml (internal standard for gas chromatograph)
- $PdCl_2$ — 2.5 mmols
- CO — 1500 psig
- Temperature — 120° C

TABLE II

EFFECT OF PHOSPHINE

| Phosphine, mmol | | L/Pd | Time, Hours | Conv., % | Selectivity Mol % | I.D. No. | Ex. No. |
|---|---|---|---|---|---|---|---|
| (Cl—⌬—)₃P | 4.6 | 1.8 | 2 | 54.5 | 14.8 | B2408-38 | 8 |

TABLE II-continued
EFFECT OF PHOSPHINE

| Phosphine, mmol | | L/Pd | Time, Hours | Conv., % | Selectivity Mol % | I.D. No. | Ex. No. |
|---|---|---|---|---|---|---|---|
| (⌬)₃P with CH₃ | 9.2 | 3.7 | 2 | 0 | 0 | B2408-37 | 9 |
| ([CH₃]₂N—⌬)₃P | 4.6 | 3.7 | 2 | 0 | 0 | B2408-40 | 10 |
| φ₂PCH₂CH₂Pφ₂ | 4.6 | 1.8 | 2 | 2.6 | 0 | B2408-15 | 11 |
| (φO)₃P | 9.2 | 3.7 | 2 | 7.6 | Trace | B2408-11 | 12 |
| (φO)₃P | 9.2 | 3.7 | 15.3 | 8.5 | Trace | B2408-35* | 13 |
| (nC₄H₉O)₃P | 9.2 | 3.7 | 2 | 1.4 | 0 | B2408-36 | 14 |
| (nC₄H₉)₃P | 9.2 | 3.7 | 2 | 6.6 | 0 | B2408-13 | 15 |
| (NCCH₂CH₂)₃P | 9.2 | 3.7 | 2 | 16.7 | 0 | B2408-17 | 16 |

*Temperature 140° C

Reactor charge:
Acetic acid 100 ml
N-acetyl-allylamine 0.5 mol
Benzene 30 ml
PdCl₂ 2.5 mmols
Phosphine as shown
Pressure 1500 psig
Temperature 120° C

TABLE III
EFFECT OF ACETYL GROUP

| Catalyst (mmol) | Feed (mol) | Gas | Additive | Temp., °C | Time, Hours | Conv., % | Selectivity Mol % | I.D. No. | Ex. No. |
|---|---|---|---|---|---|---|---|---|---|
| PdCl₂ φ₃P (2.5) (9.2) | * (0.5) | CO | — | 160 | 16.25 | 100 | 0 | B2352-29 | 17 |
| PdCl₂ φ₃P (2.5) (9.2) | ** (0.25) | CO | HO—⌬—OH | 120 | 2 | 95.7 | 45.2 | B2352-39 | 18 |
| PdCl₂ φ₃P (2.5) (none) | ** (0.25) | CO | — | 120 | 2 | 7.0 | 0 | B2352-49 | 19 |

*allylamine
**N-acetyl-allylamine

Reactor charge:
Acetic acid 50 ml (100 ml in Ex. 17)
Benzene 0.25 mol (0.5 in Ex. 17)
Catalyst As shown
CO pressure 1500 psig

TABLE IV
EFFECT OF SOLVENT

| Solvent | Time, Hours | CO mol | Conv., % | Selectivity mol % | I.D. No. | Ex. No. |
|---|---|---|---|---|---|---|
| Acetic acid | 2 | 0.32 | 95.7 | 45.2 | B2352-39 | 20 |
| CH₃CON(CH₃)₂ | 2 | 0.14 | 83.5 | 8.3 | B2352-43 | 21 |
| CH₃CN | 19.3 | 0.17 | 57.8 | 8.9 | B2352-45 | 22 |
| φCH₃ | 2 | 0.14 | 57.5 | 11.0 | B2352-44 | 23 |

Reactor charge:
Solvent 100 ml.
N-acetyl-allylamine 0.5 mol
Benzene 30 ml
PdCl₂ 2.5 mmol
φ₃P 9.2 mmol
CO pressure 1500 psig
Temperature 120° C

TABLE V
CARBONYLATION OF N-ACETYL-ALLYLAMINE — EFFECT OF PHOSPHINE

| Phosphine | mmol | L/Pd | Time, Hours | Conv.,% | Selectivity mol % | I.D. No. | Ex. No. |
|---|---|---|---|---|---|---|---|
| φ₃P | 30 | 13.3 | 2 | 92.8 | 61.6 | B2532-14 | 24 |
| φ₃P | 90 | 36.0 | 2 | 84.0 | 64.9 | B2532-05 | 25 |
| φ₂(nC₄H₉)P | 4.6 | 3.7 | 2 | 30.7 | 21.8 | B2463-48 | 26 |
| φ₂(nC₄H₉)P | 16.7 | 13.3 | 6 | 100 | 61.2 | B2463-50 | 27 |
| φ₂(ethoxy)P | 4.6 | 3.7 | 2 | 3.1 | 0 | B2463-47 | 28 |
| (pCH₃φ)₃P | 4.6 | 3.7 | 2 | 51.9 | 29.7 | B2532-08 | 29 |
| (pCH₃φ)₃P | 16.7 | 13.3 | 4 | 98.2 | 54.3 | B2532-12 | 30 |
| (pCH₃Oφ)₃P | 4.6 | 3.7 | 2 | 25.2 | 29.6 | B2532-02 | 31 |
| (pCH₃Oφ)₃P | 16.7 | 13.3 | 10 | 97.1 | 55.9 | B2532-03 | 32 |
| (φCH₂)₃P | 4.6 | 3.7 | 2 | 57 | 0 | B2532-11 | 33 |

Reactor Charge:
Acetic acid 50 ml
N-acetyl-allylamine 0.25 mol
Benzene 15 ml
Phosphine As shown
PdCl₂ 1.25 mmols

TABLE VI
CARBONYLATION OF N-ACETYL-ALLYLAMINE — EFFECT OF CATALYST

| Catalyst (mmol) | Solvent | Time, Hours | Temp. °C | P, psig | ΔCO mol | Conv., % | Selectivity mol % | I.D. No. | Ex. No. |
|---|---|---|---|---|---|---|---|---|---|
| PdCl - $\phi_3$P (1.125) (200) | P | 4 | 120 | 1000 | .107 | 34.3 | 52.1 | B2532-21 | 34 |
| PdCl - $\phi_3$P - HOAc (1.125) (200) (166) | P | 4 | 120 | 1000 | .053 | 40.4 | 71.0 | B2532-46 | 35 |
| PdCl - $\phi_3$P (2.25) (30) | HOAc | 2 | 120 | 1040 | .250 | 84.3 | 45.3 | B2532-47 | 36 |
| 5% Pd/C-$\phi_3$P | HOAc | 2 | 120 | 1040 | .303 | 84.6 | 45.8 | B2607-03 | 37 |
| PtCl$_2$ - $\phi_3$P | HOAc | 16.75 | 120 | 1150 | .304 | 66.8 | 62.3 | B2607-04 | 38 |
| PtCl$_2$ - $\phi_3$P | P | 16.50 | 120 | 1000 | — | 2.7 | 0 | B2607-15 | 39 |
| RuCl$_3$ - $\phi_3$P (1.12) (4.6) | HOAc | 15.25 | 120 | 1060 | 0 | 1.5 | 0 | B2607-05 | 40 |
| Rh(AcAc)$_3$ - (n-C$_4$H$_9$)$_3$P (0.5) (1.25) | neat | 16.0 | 140 | 1050 | 0 | 39.2 | 0 | B2607-17 | 41 |
| CO$_2$(CO)$_8$ | HOAc | 6 | 250 | 2800 | 0 | 74.0 | 0 | B2607-22 | 42 |
| CO$_2$(CO)$_8$ - $\phi_3$P (5.5) (15) | HOAc | 6 | 250 | 2800 | 0 | 78.0 | 0 | B2607-22 | 43 |
| Ni(CO)$_4$ (200) | neat | 16 | 200 | 2000 | 0 | 8.4 | 0 | B2607-20 | 44 |

Reactor charge:
- Solvent: 120 ml
- N-acetyl-allylamine: 0.5 mol
- Benzene: 30 ml (internal standard)
- Catalyst: As shown

TABLE VII
CARBONYLATION OF N-ACETYL-ALLYLAMINE IN MOLTEN PHOSPHINE

| PdCl$_2$, mmol | L/Pd | Temp., °C | Time, Hours | ΔCO, mol | Conv., % | Selectivity mol % | I.D. No. | Ex. No. |
|---|---|---|---|---|---|---|---|---|
| 2.25 | 178 | 120 | 4 | 0.107 | 34.3 | 52.1 | B2532-21 | 45 |
| 2.25 | 178 | 120 | 15.5 | 0.214 | 50 | 62.5 | B2532-25 | 46 |
| 2.25 | 178 | 120 | 15.5 | 0.161 | 42.2 | 70.5 | B2532-28 | 47 |
| 2.25 | 178 | 140 | 15 | 0.161 | 42.6 | 82.0 | B2532-30 | 48 |
| 3.0 | 44.5 | 100 | 16 | 0.268 | 62.8 | 67.1 | B2532-35 | 49 |
| 3.0 | 44.5 | 120 | 15.5 | 0.411 | 97.4 | 70.2 | B2532-34 | 50 |
| 3.0 | 44.5 | 140 | 2 | 0.357 | 96.4 | 60.0 | B2532-33 | 51 |
| 4.5 | 44.5 | 140 | 16.75 | 0.196 | 93.0 | 68.7 | B2532-31 | 52 |

Reactor charge:
- $\phi_3$P: 104 g (0.4 mol)
- N-acetyl-allylamine: 50 g (0.5 mol)
- PdCl$_2$: As shown

TABLE VIII
CARBONYLATION OF SUBSTITUTED ALLYLAMINES

| Allylamine (mol), Solvent | Catalyst (mmol) | Time, Hours | ΔCO mol | Conv.,% | Selectivity mol % | I.D. No. | Ex. No. |
|---|---|---|---|---|---|---|---|
| N-acetyl-allyamine, Acetone (0.25) | H$_2$PtCl$_2$·6H$_2$O-SnCl$_2$·2H$_2$O (2.5)15.100 (12.5) | 3 | .089 | 68.5 | 30.5 | B2607-25 | 53 |
| N-acetyl-allylamine, Acetic Acid (0.25) | H$_2$PTCl$_2$·6H$_2$O-SnCl$_2$·2H$_2$O (2.5) (12.5) | 6 | .071 | 39.8 | 45.8 | B2607-30 | 54 |
| Allylamine, Triethylamine (0.25) | PdCl$_2$-$\phi_3$P (1.125) (15) | 16.5 | 0 |  | 0 | B2607-32 | 55 |
| N-phenyl-allylamine, Acetic Acid (0.25) | PdCl$_2\phi_3$P (1.125) (15) | 6 | — | 0 | 0 | B2607-24 ? | 56 |
| C=C—C—NHCNH, Acetic Acid (0.25) (with C=O) | PdCl$_2$, $\phi_3$P (1.125) (15) | 17.5 | 0 |  |  | B2607-23 | 57 |
| C=C—C—NHCNH, $\phi_3$P (with C=O) | PdCl$_2$-$\phi_3$P (1.125) (15) | 6 |  | 0 | 0 | B2607-27 | 58 |

Reactor charge:
- Solvent: 50 ml
- Feed: 0.25 mol
- Internal Standard: 15 ml
- Catalyst: As shown
- Temperature: 120° C

What is claimed is:

1. A process for producing N-acetyl-2-pyrrolidone which comprises:
   (a) reacting allylamine with acetic acid to thereby obtain N-acetyl-allylamine; and
   (b) contacting the N-acetyl-allylamine with a catalyst of palladium or platinum, coordinated with an aryl phosphine selected from the group consisting of triphenylphosphine; diphenyl-n-butyl phosphine; tri-(p-methylphenyl)-phosphine and tri-(p-methoxyphenyl)-phosphine, and carbon monoxide in the presence of acetic acid and in the absence of water in a reaction zone, at a temperature between 50° and 200° C and a carbon monoxide partial pressure above 100 psig.

2. A process for producing N-acetyl-2-pyrrolidone which comprises: (a) reacting allylamine with acetic acid to thereby obtain N-acetyl-allylamine; and (b) contacting the N-acetyl-allylamine with a triphenylphosphine-coordinated palladium or platinum catalyst and carbon monoxide in the presence of acetic acid and in the absence of water in a reaction zone, at a temperature between 50° and 200° C and a carbon monoxide partial pressure above 100 psig.

3. A process in accordance with claim 2 wherein steps (a) and (b) are carried out in the same reaction zone.

4. A process in accordance with claim 2 wherein steps (a) and (b) are carried out in separate reaction zones.

5. A process in accordance with claim 2 wherein the step (b) contacting is carried out in the presence of acetic acid anhydride to thereby maintain anhydrous conditions in the reaction zone.

* * * * *